(12) United States Patent
Dankert et al.

(10) Patent No.: US 7,584,669 B2
(45) Date of Patent: Sep. 8, 2009

(54) METHOD FOR RECORDING MICROSTRUCTURAL CHANGES IN A COMPONENT

(75) Inventors: Michael Dankert, Offenbach (DE); Martin Feldhege, Saarlouis (DE); Stefan Irmisch, Jupiter, FL (US); Matthias Oechsner, Mülheim an der Ruhr (DE); Eckart Schumann, Mülheim an der Ruhr (DE); Werner Stamm, Mülheim an der Ruhr (DE)

(73) Assignee: Siemens Aktiengesellschaft, Munich (DE)

( * ) Notice: Subject to any disclaimer, the term of this patent is extended or adjusted under 35 U.S.C. 154(b) by 132 days.

(21) Appl. No.: 10/589,791

(22) PCT Filed: Feb. 14, 2005

(86) PCT No.: PCT/EP2005/001469

§ 371 (c)(1),
(2), (4) Date: Aug. 17, 2006

(87) PCT Pub. No.: WO2005/080937

PCT Pub. Date: Sep. 1, 2005

(65) Prior Publication Data

US 2007/0180897 A1    Aug. 9, 2007

(30) Foreign Application Priority Data

Feb. 17, 2004  (EP) .................... 04003538

(51) Int. Cl.
*G01N 3/00* (2006.01)
(52) U.S. Cl. ......................................... 73/788
(58) Field of Classification Search ............ 73/788, 73/786
See application file for complete search history.

(56) References Cited

U.S. PATENT DOCUMENTS

| | | | | |
|---|---|---|---|---|
| 3,733,887 | A | * | 5/1973 | Stanley et al. ............ 374/44 |
| 4,408,294 | A | | 10/1983 | Imam |
| 4,794,797 | A | * | 1/1989 | Ogawa ................. 73/786 |
| 5,552,711 | A | | 9/1996 | Deegan et al. |
| 5,588,034 | A | | 12/1996 | Bowen et al. |
| 5,831,299 | A | * | 11/1998 | Yokoyama et al. ....... 257/295 |
| 6,024,792 | A | | 2/2000 | Kurz et al. |
| 6,025,078 | A | * | 2/2000 | Rickerby et al. ......... 428/469 |

(Continued)

FOREIGN PATENT DOCUMENTS

DE            24 42 639 A1      1/1976

(Continued)

*Primary Examiner*—Lisa M Caputo
*Assistant Examiner*—Octavia Davis

(57) ABSTRACT

Method for recording microstructural changes in a layer system component. A specific material parameter of the component is measured. The layer system may include an alloy substrate and an alloy or porous ceramic layer. The material parameter may be measured a plurality of times. The measured material parameter may include electrical capacitance, specific heat capacity, peltier coefficient or magnetic susceptibility. The material parameter may first be measured on a new component and subsequent measurements may be performed at a time interval after operational use. The recorded material parameter is then used to determine microstructural changes in the substrate or the layer material of the component caused by changes in precipitation, cracks, or depletion of an alloying element.

19 Claims, 10 Drawing Sheets

U.S. PATENT DOCUMENTS

| | | | |
|---|---|---|---|
| 6,200,088 B1 | 3/2001 | Zombo et al. | |
| 6,333,118 B1 * | 12/2001 | Alperine et al. | 428/469 |
| 6,455,173 B1 | 9/2002 | Marijnissen et al. | |
| 6,512,379 B2 | 1/2003 | Harrold et al. | |
| 6,517,236 B2 | 2/2003 | Sun et al. | |
| 6,544,665 B2 | 4/2003 | Rigney et al. | |
| 6,553,318 B2 | 4/2003 | Mansky | |
| 6,577,141 B2 | 6/2003 | Gandrud | |
| 6,635,362 B2 * | 10/2003 | Zheng | 428/678 |
| 6,668,230 B2 * | 12/2003 | Mansky et al. | 506/39 |
| 6,686,060 B2 * | 2/2004 | Bruce et al. | 428/633 |
| 6,887,588 B2 * | 5/2005 | Ackerman et al. | 428/633 |
| 6,960,395 B2 * | 11/2005 | Spitsberg et al. | 428/632 |
| 6,968,730 B2 * | 11/2005 | Schafrik et al. | 73/105 |
| 6,979,498 B2 * | 12/2005 | Darolia et al. | 428/633 |
| 6,982,126 B2 * | 1/2006 | Darolia et al. | 428/701 |
| 7,010,987 B2 * | 3/2006 | Antonelli et al. | 73/799 |
| 7,087,266 B2 * | 8/2006 | Darolia et al. | 427/255.32 |
| 7,150,798 B2 * | 12/2006 | Schnell et al. | 148/509 |
| 7,309,530 B2 * | 12/2007 | Spitsberg et al. | 428/632 |

FOREIGN PATENT DOCUMENTS

| | | |
|---|---|---|
| EP | 0 773 359 A1 | 5/1997 |
| EP | 0 892 090 A1 | 1/1999 |
| EP | 1 204 776 B1 | 5/2002 |
| EP | 1 306 454 A1 | 5/2003 |
| EP | 1 319 729 A1 | 6/2003 |
| WO | WO 99/67435 A1 | 12/1999 |
| WO | WO 00/44949 A1 | 8/2000 |
| WO | WO 02/079774 A2 | 10/2002 |

* cited by examiner

METHOD FOR RECORDING MICROSTRUCTURAL CHANGES IN A COMPONENT

CROSS REFERENCE TO RELATED APPLICATIONS

This application is the U.S. National Stage of International Application No. PCT/EP2005/001469, filed Feb. 14, 2005 and claims the benefit thereof. The International Application claims the benefits of European Patent application No. 04003538.8 filed Feb. 17, 2004. All of the applications are incorporated by reference herein in their entirety.

FIELD OF THE INVENTION

The invention relates to a method for recording microstructural changes in a component as claimed in the claims.

BACKGROUND OF THE INVENTION

Components which are exposed to mechanical and/or thermal stresses reveal degradation in their mechanical, chemical or thermal properties, because their microstructure changes on account of the stresses. Components in turbines, such as for example gas or steam turbines, are exposed to both mechanical and thermal stresses. Components of this type are configured as a layer system in particular in the combustion chamber or in the first stage of the turbine. In this case, one or more interlayers are present on a substrate, i.e. a supporting structure, with these interlayers protecting the component from oxidation/corrosion and excessive introduction of heat.

A ceramic layer is used as a thermal barrier.

U.S. Pat. No. 6,200,088 and U.S. Pat. No. 6,455,173 disclose that components are monitored in operation.

U.S. Pat. No. 6,544,665 discloses the sintering of a thermal barrier coating.

U.S. Pat. No. 6,553,318 B2 discloses a method for quickly and simultaneously measuring properties of a large number of specimens.

U.S. Pat. No. 6,577,141 B2 discloses a capacitive method for determining the density of asphalt.

U.S. Pat. No. 6,512,379 B2 discloses an apparatus for monitoring the state of a thermal barrier coating, in which electricity is generated intrinsically within the thermal barrier coating, for example by a piezo effect.

U.S. Pat. No. 4,408,294 A discloses a method for detecting cracks which form as a result of vibrations.

EP 0 773 359 A1 discloses an apparatus for monitoring damage to ceramic parts, in which electrical conductor tracks used as detectors are additionally introduced.

WO 02/079774 A2 discloses a nondestructive testing method using an eddy current measurement method.

U.S. Pat. No. 5,552,711 A discloses a monitoring system in which electromagnetic signals from ions are recorded, these ions originating from worn components.

U.S. Pat. No. 5,588,034 A discloses an apparatus and a method for examining a crystal by means of X-rays.

DE 24 42 639 A discloses a method for monitoring the erosion state of gas turbine blades or vanes which uses a resistance of a comparison body to conduction to determine the state of erosion.

U.S. Pat. No. 6,517,236 B2 discloses a thermography method.

Hitherto, the microstructure of some components of an apparatus comprising a large number of components had to be subjected to destructive examination in order to be able to decide whether the other, remaining components can remain in use.

SUMMARY OF THE INVENTION

Therefore, it is an object of the invention to overcome this problem.

The object is achieved by a method for recording the microstructural changes in a component according to the claims by material parameters of the component being determined at least twice and in particular more than twice by means of suitable measurement methods.

The subclaims list further advantageous measures and variants of the method according to the invention. The measures listed in the subclaims can be combined with one another in advantageous ways.

In the measurement methods used in accordance with the invention, energy has to be introduced into the material from the outside in the form of electric voltage, heat or mechanical energy in order to obtain a measurement signal. This contrasts with U.S. Pat. No. 6,512,379, in which electricity is formed within the thermal barrier coating without any external action.

Unlike in EP 0 773 359 A1, no additional measures are taken, for example in the form of the provision of conductor tracks, to enable a measurement method to be carried out.

A thermography examination is not possible for the components described in the present application, as per U.S. Pat. No. 6,517,236 B2, since the components cannot be heated from a rear side.

DETAILED DESCRIPTION OF THE INVENTION

Figure 1:
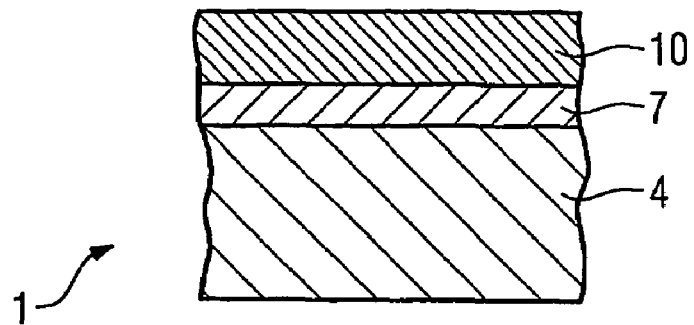
FIG. 1 shows a layer system.

FIG. 1 shows, by way of example, a component 1 which is designed as a layer system 1.

The layer system 1 comprises a substrate 4, to which at least one layer 7 has been applied. By way of example, a further outer layer 10 has been applied to this layer 7, which then constitutes an interlayer.

The substrate 4 may be metallic or ceramic. In particular in the case of components for turbomachines (aircraft engines, turbines for power generation, compressors, such as for example gas turbines 100 (FIG. 18) or steam turbines 300, 303 (FIG. 17)), such as for example turbine blades or vanes 120, 130 (FIG. 19), housing parts or combustion chamber linings 155 (FIG. 20), the substrate 4 is metallic and preferably consists of an iron-base, cobalt-base or nickel-base superalloy.

A bonding layer, in particular a metallic layer 7, for example a MCrAlX layer, in which M stands for at least one element selected from the group consisting of iron, cobalt or nickel and X stands for yttrium, silicon and/or at least one rare earth element (active elements), may be present on the substrate 4.

The outer layer may once again be metallic or ceramic. In the case of turbine components 120, 130, 155, the outer layer 10 is often a ceramic thermal barrier coating.

Further structural forms of a layer system 1 are conceivable. By way of example, a ceramic layer can be applied direct to the substrate 4. In particular, there is no need to provide a ceramic thermal barrier coating 10 for components which are used at locations of a turbine 100, 300, 303 that are not excessively hot, in which case the layer 7 already constitutes the outer layer.

The method according to the invention can also be employed for a component 1 which comprises only a substrate 4.

Microstructural changes result, inter alia, from
a) cracks,
b) pores,
c) phase changes (lattice structure),
d) change in the chemical composition,
e) change in the precipitations,
f) stresses (residual stresses).

Figure 2:
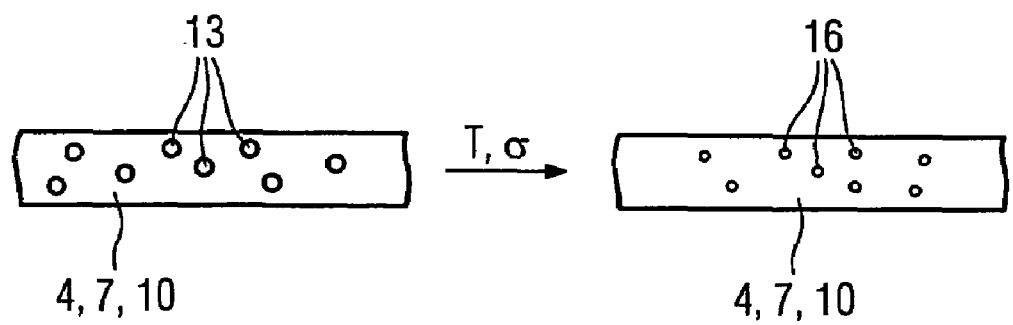
FIG. 2 shows microstructural changes to a layer or a substrate of a layer system.

FIG. 2 shows an example of a microstructural change in a substrate 4 and/or a layer 7, 10 of a layer system 11.

The ceramic thermal barrier coating 10 mentioned here by way of example is intended to have good thermal shock properties, achieved in particular by a certain porosity. Therefore, pores 13 of a certain size are present in the layer 10 (FIG. 2, left). On account of operational use of the layer 10, for example in the turbine 100, 300, 303, the thermal barrier coating 10 is subject to the introduction of heat and/or mechanical stresses σ. On account of the influence of the temperature T and/or mechanical stresses σ, the porous thermal barrier coating 10 sinters together, so that the larger pores 13 become smaller pores 16 (FIG. 2, right). The reduction in the size of the pores 13 reduces the porosity, which has an adverse effect on the thermal shock properties of the ceramic thermal barrier coating 10.

Figure 3:
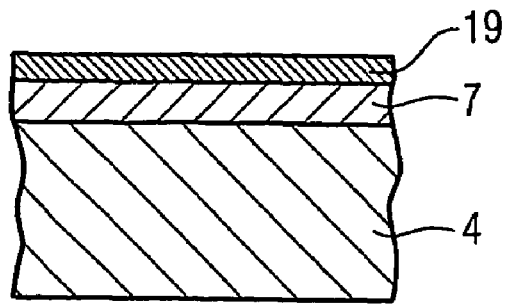
FIG. 3 shows degradation of a coated substrate caused by oxidation.

The microstructural change, in this case the porosity, therefore causes a deterioration in the thermal shock properties. FIG. 3 shows the microstructural changes in a metallic protective layer 7 on a substrate 4.

For example in the case of the MCrAlX layers (FIG. 18), an aluminum oxide layer 19, or in more general terms an oxide or corrosion layer 19, forms on a protective layer 7 which serves as an oxidation-resistant or corrosion-resistant layer. Depending on the alloy used, therefore, depletion of an element of an alloy of the layer 7 or of the substrate 4 which forms an oxide or corrosion product occurs. In the case of the MCrAlX layer 7, aluminum is depleted in the MCrAlX layer 7 beneath the layer 19.

The layer 7 may also be an aluminized or chromed region of the substrate 4. In this case, aluminum and/or chromium was applied to the substrate 4 and left to diffuse in.

The substrate 4 is then enriched with aluminum or chromium. In this case too, the formation of aluminum oxide or chromium oxide leads to depletion of aluminum or chromium on account of oxidation or corrosion.

Figure 4:
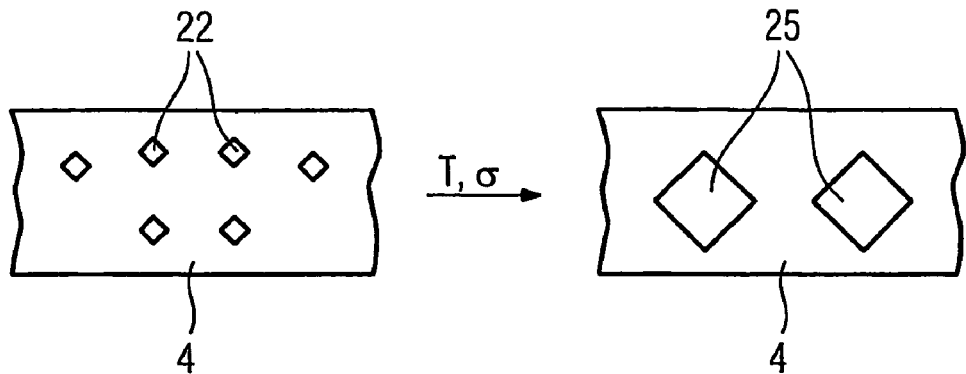
FIG. 4 shows microstructural changes to a substrate of a layer system.

FIG. 4 shows a further microstructural change in a layer system, in particular the substrate 4.

A substrate 4 of this type, in particular made from a superalloy, has precipitations 22 (γ' phase) which have a positive influence on the mechanical properties (FIG. 4, left).

On account of the temperature T and/or stresses σ, the precipitations 22 change in such a way that the positive influence on the mechanical properties is at least considerably reduced. This occurs through an increase in the size of the precipitations 25 (FIG. 4, right).

Cracks may likewise be present in the substrate 4 and/or in the layers 7, 10, increasing the porosity.

Since there are no direct, unique parameters for the microstructure (cracks, pores, precipitations, etc.), the microstructure is integrally determined indirectly by means of one or more material parameters which are influenced by cracks, pores and precipitations, etc. The measurements are, for example, non-destructive measurements.

Figure 5:
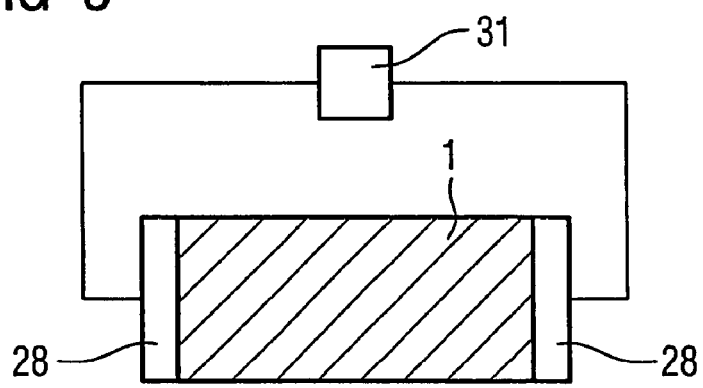
FIGS. 5, 6, 7, 8, 9, 10, 11, 12 13, 14, 15 show various examples of measurement arrangements for determining material parameters of a layer system.

FIG. 5 shows an example of a measurement arrangement for determining a material parameter of the substrate 4 and/or of the layer 7, 10. In this case, electrodes 28 are applied at suitable locations of the substrate 4 or the layer 7, 10. The electrical capacitance C[F] can be determined by means of a measurement appliance 31.

The capacitance measurement is most suitable if the substrate 4 or the layer 7, 10 consists of ceramic, i.e. has a high dielectric constant $\in$, and a reduction in the porosity is expected.

Figure 6:
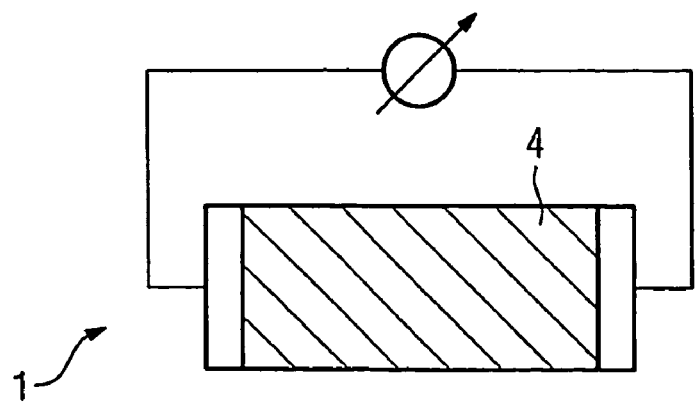
Figure 7:
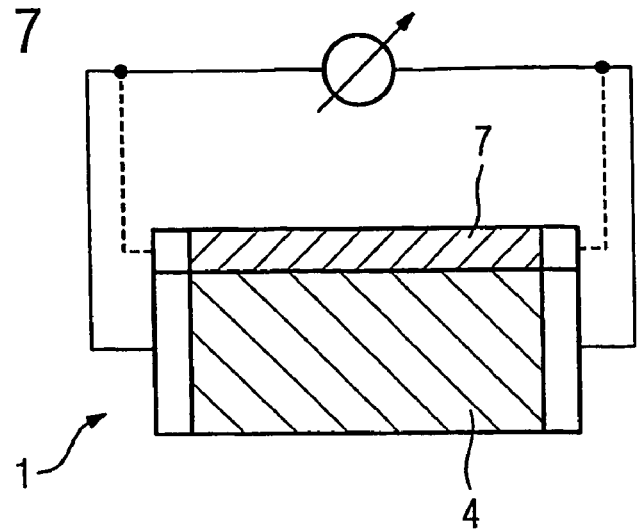

The material parameters of the substrate 4 can be measured if the layers on top have been removed (FIG. 6) but also if the layers 7 on top are still present (FIG. 7).

As an alternative to the capacitance, it is also possible to determine other electrical properties, the ferroelectric properties and the pyroelectric properties, in particular of a ceramic.

Figure 8:
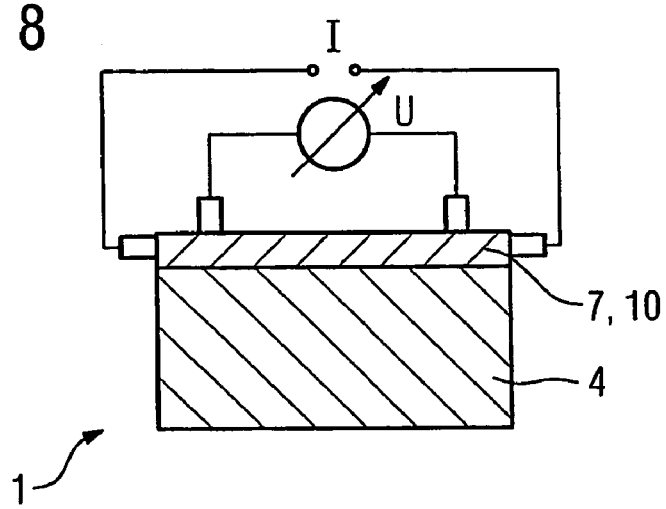

FIG. 8 shows a further example of a measuring arrangement for determining a material parameter of a layer 7, 10.

By way of example as a result of the depletion of the aluminum content in the layer 7 (FIG. 3), the electrical conductivity σ changes, which can be determined for example by means of a 4-point method. Further material parameters which can be measured in order to ascertain the chemical change to the microstructure include the thermal conductivity or magnetic properties.

In the 4-point method, a constant current I (direct current) is applied at two locations of the layer 7 or the substrate 4. The voltage drop U is tapped off at two locations located between the current contact-connection points. This information is used to determine a resistance $$R = \frac{U}{I}(\sigma \sim 1/R).$$

The electrical conductivity can also be determined by means of inductive resistance (alternating current).

A change in the microstructure can be determined by means of electrical and/or electromagnetic material values. These are once again the electrical conductivity, an inductive resistance and/or magnetic properties, such as the susceptibility.

Figure 9:
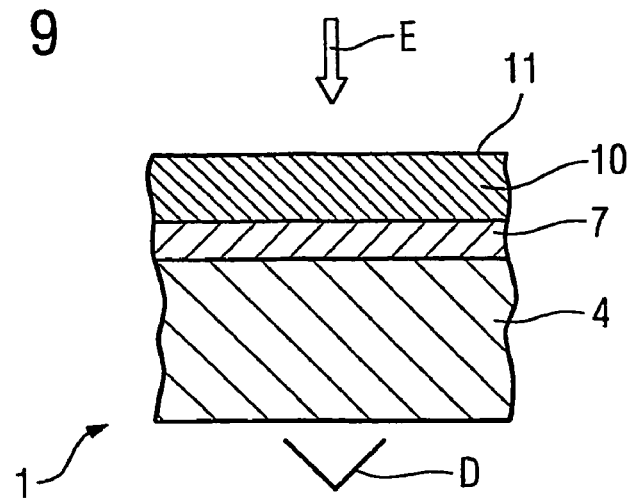

FIG. 9 shows another way of determining a material parameter of the ceramic thermal barrier coating 10.

In this case, the thermal conductivity λ of the layer 10 is determined. This is done by a laser flash method or by a thermal wave analysis.

In the laser flash method, a brief introduction of heat E is introduced on the outer side 11 of the layer 10. The thermal conductivity λ of the thermal barrier coating 10 is determined by the heat E introduced in this way being distributed over the entire specimen after a certain time and leading to heating of the rear side of the specimen and of the interlayer 7 of the substrate 4. The time profile determines the temperature conductivity λ. The heating is measured using an infrared detector D or a pyrometer D.

The layer thickness of the layer 10 can be determined in advance (eddy current method), since the layer thickness of the layer 10 may change in use as a result of erosion. The possibly reduced layer thickness is taken into account in the calculation of the thermal conductivity.

The change in the chemical composition of the intermediate protective layer 7 also alters the time profile of the heating, since in this case the thermal conductivity of the intermediate protective layer 7 has also changed.

In the case of thermal wave analysis, the specimen to be tested is exposed to an intensity-modulated light beam, generally a laser beam. As a result of the absorption of this radiation with the intensity I in the specimen surface, the energy of the electromagnetic field, which dissipates into heat, generates a time-dependent temperature field T which comprises a temperature field that is constant over the course of time and a time-modulated temperature field. This time-variable temperature field component is referred to as the thermal wave. The modulation frequency W and its phase shift F, with which the thermal wave follows its excitation, are characteristic of the thermal wave. It results as a solution of the inhomogeneous heat conduction equation.

The propagation of this damped thermal wave is dependent on the specimen properties to be measured, such as for example thermal conductivity.

A change in the microstructures of the two layers 7, 10 can be recorded by comparison measurements on a layer assembly made up of thermal barrier coating 10 and intermediate protective layer 7.

The specific heat capacity can also be determined as the material parameter.

Figure 10:
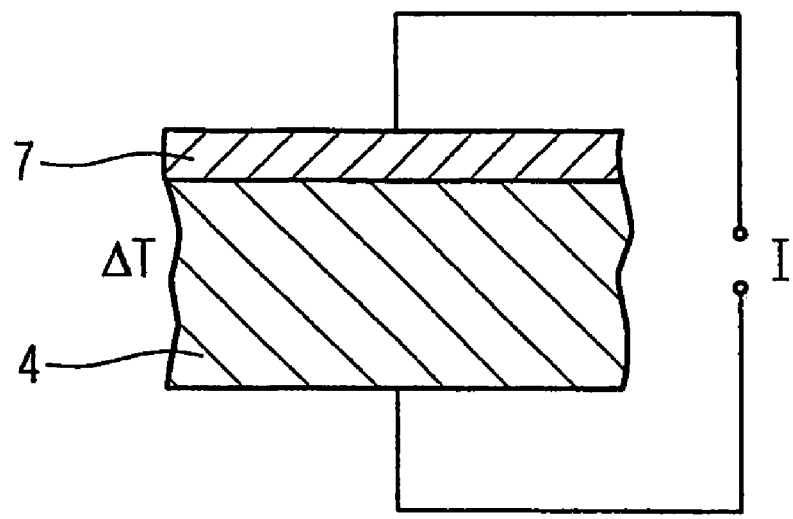
Figure 11:
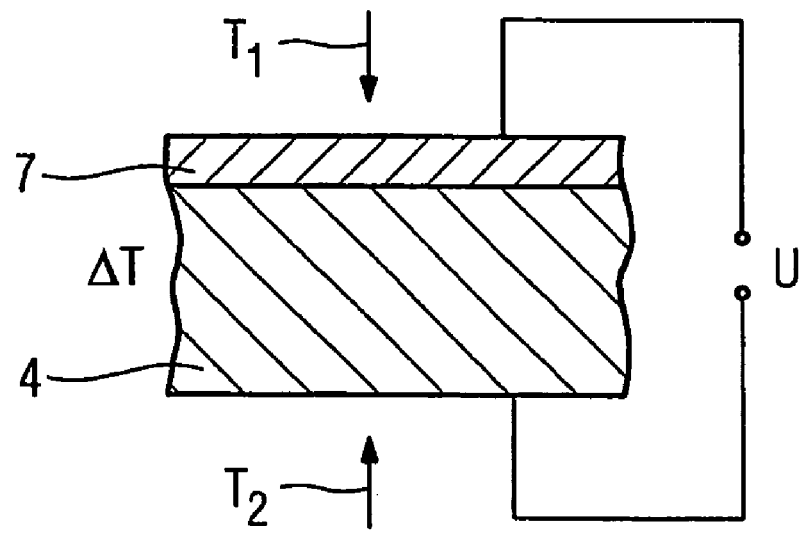

It is also possible to utilize the Peltier effect to record the material changes. In the Peltier effect, an electric current I flows through the metallic layer 7 and the metallic substrate 4, with the result that a temperature difference ΔT is generated between substrate 4 and layer 7 (FIG. 10). The temperature difference ΔT is dependent on the materials of the substrate 4 and the layer 7. The reverse of the Peltier effect, i.e. the Seebeck effect, can also be utilized (FIG. 11).

In this case, an electric voltage U is generated by a temperature difference $\Delta T = T_1 - T_2$. The temperature difference ΔT is present during operation of substrate 4 and layer 7 and can be measured.

Figure 12:
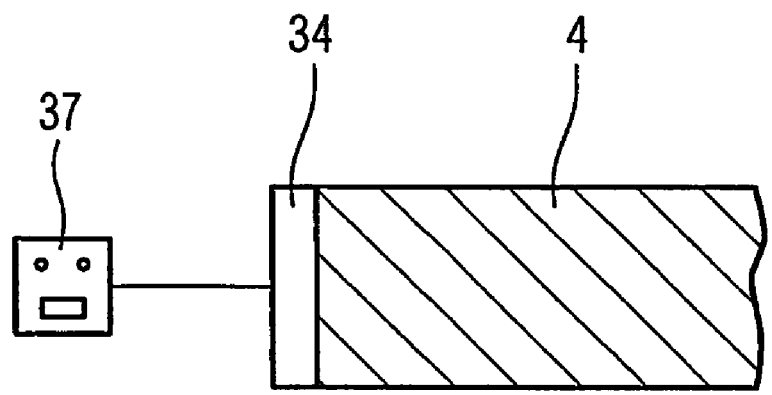
Figure 13:
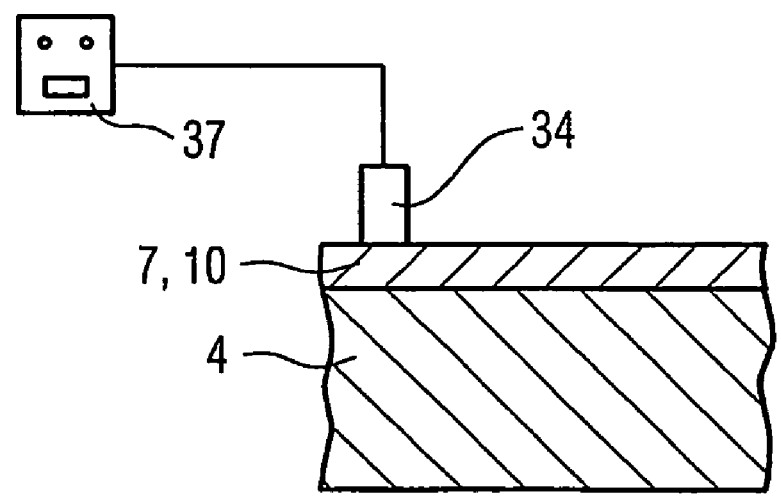

FIGS. 12, 13 show further arrangements for determining material parameters. An ultrasound probe 34 is placed onto the substrate 4 (FIG. 12) and/or onto the layer 7, 10 (FIG. 13) in order to determine the acoustic velocity in the material. The acoustic velocity depends on the mechanical E modulus and the density.

The determination of the acoustic velocity in the substrate 4 can be carried out with or without layers 7, 10 on top.

It is also possible to determine the acoustic velocity in the layers 7, 10 which are on top of the substrate 4. It is also possible to measure the acoustic velocity through the layers 7, 10 and the substrate 4.

Since the acoustic velocity depends on the E modulus and the density, the acoustic velocity is determined by a change in the porosity, formation of cracks, phase change and/or precipitations.

Figure 14:
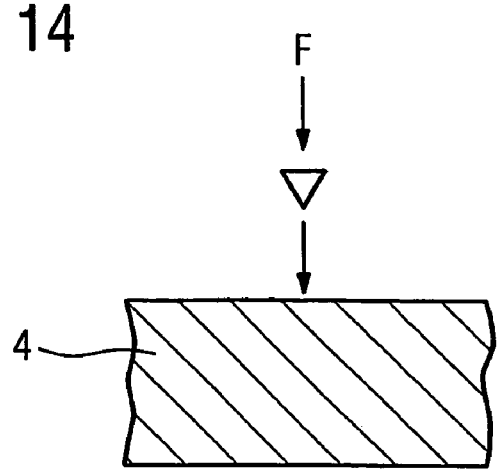
Figure 15:
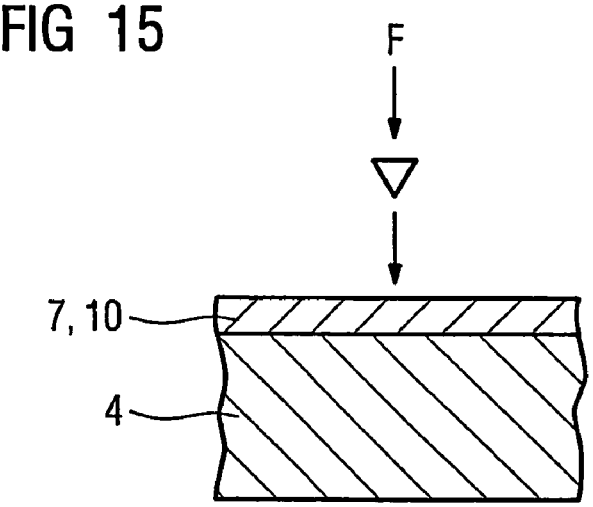

FIG. 14 shows a further arrangement for determining a material parameter. Here, the penetration depth into the substrate 4 (FIG. 14) or the layers 7, 10 (FIG. 15) is determined by means of a micro-indenter.

In this case, a specific predetermined force F of the micro-indenter is allowed to act on the surface of the substrate 4 or the layer 7, 10 for a defined time. The size of indentation depends on the E modules of the material of the substrate 4 or the layer 7, 10. The E modulus is in turn determined by an altered porosity and/or a change in precipitations.

Figure 16:
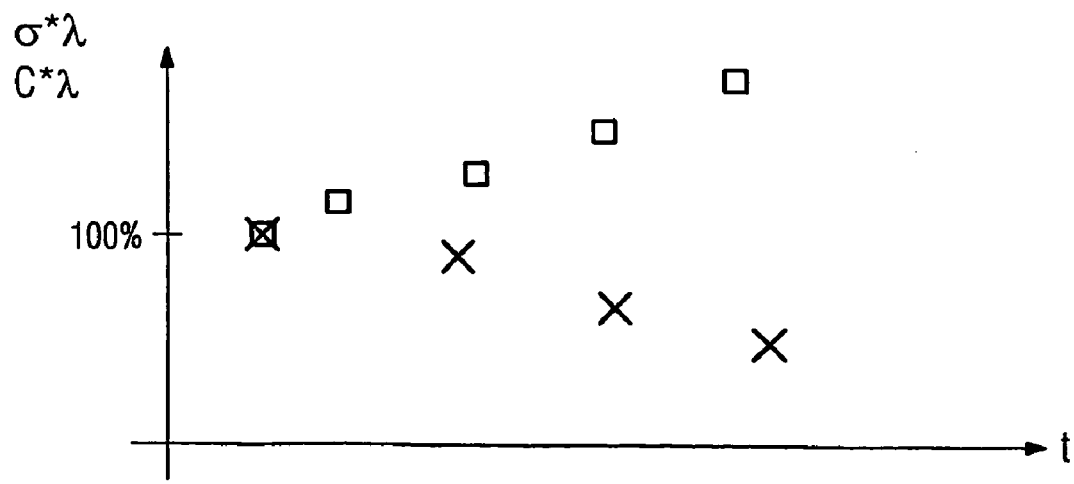
FIG. 16 shows a time profile of material parameters.

FIG. 16 shows an example of a time profile of a plurality of material parameters which are measured at various time intervals. A material parameter may drop (FIG. 16: X) or increase (FIG. 16: □) continuously or discontinuously over the course of time, because the material parameter has increased or decreased compared to the starting state.

The starting value at t=0 prior to first use is standardized to 100%, where t=0 is equated to the beginning of first use if the measurement took place for example before installation of the component 1.

All the following values of the material parameter(s) of the component 1, after it has been used, are compared with the starting value at time intervals.

Instead of one parameter, it is also possible to determine two or more parameters which are plotted, for example, as a product or quotient, i.e. for example capacitance times thermal conductivity λ (FIG. 16, C*λ) or electrical conductivity times thermal conductivity (FIG. 16, σ*λ).

The formation of a product is suitable if the material parameters evolve in a similar way over the course of time, i.e. either increase or decrease. The formation of a quotient is appropriate in the event of opposite evolution over the course of time.

Similar profiles to those illustrated in FIG. 16 also result for the time profile of a single parameter.

On the basis of predetermined calibration curves, a microstructural change can be recorded as a function of time on the basis of the change in the material parameter.

Comparison specimens or newly produced components which have an as yet undegraded microstructure, and comparison specimens or components which have been used and constitute a degraded microstructure, for which replacement or renewal of the component is recommended, are used to determine a time when a real component needs to be tested or refurbished or has reached the end of its service life. The comparison specimens may also be real components 1.

The at least second or subsequent measurements are carried out at a time interval after the first measurement, after or during initial operational use. The measurement of the material parameters can take place on line and in automated fashion. For example, the microstructural state of the component 1 can be checked at any time.

Beyond a certain percentage change, i.e. after a certain duration of time following t=0, it is possible to determine from when a component 1 needs to be refurbished or completely replaced. By way of example, it is suitable to provide for maintenance when it can be recognized that refurbishment of components 1 is still possible but delaying the maintenance means that refurbishment appears less economically viable.

The material parameters can be measured while the component 1 is in use.

If this is not possible, the measurement can also take place when the component 1, for example a turbine blade or vane 120, 130, is still installed in an apparatus which is not in operation, for example a turbine 100, 300, 303.

Figure 17:
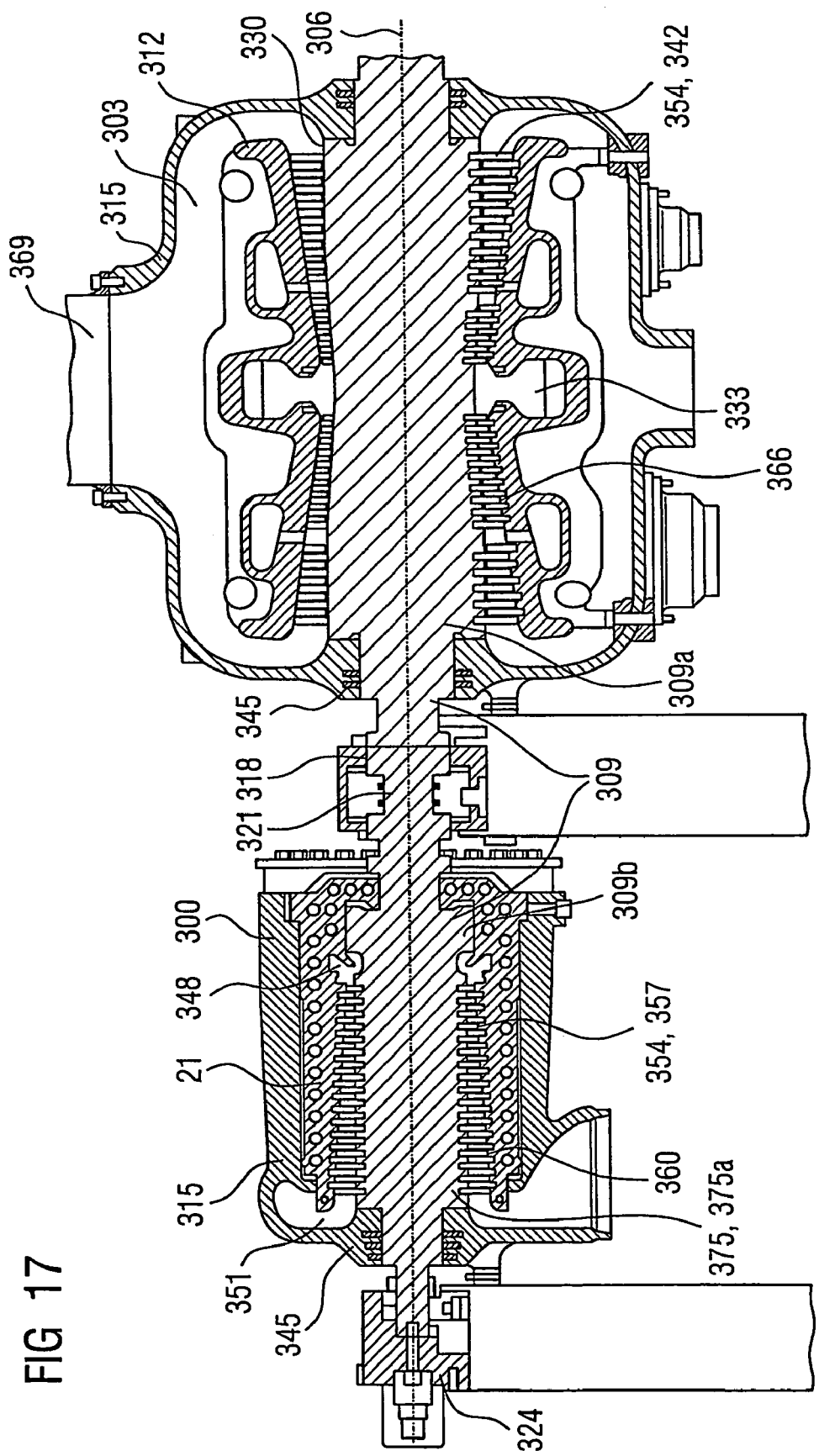
FIG. 17 shows a steam turbine.

FIG. 17 illustrates, by way of example, a steam turbine 300, 303 with a turbine shaft 309 extending along an axis of rotation 306.

The steam turbine has a high-pressure part-turbine 300 and an intermediate-pressure part-turbine 303, each with an inner casing 312 and an outer casing 315 surrounding it. The high-pressure part-turbine 300 is, for example, of pot-type design. The intermediate-pressure part-turbine. 303 is of two-flow design. It is also possible for the intermediate-pressure part-turbine 303 to be of single-flow design. Along the axis of rotation 306, a bearing 318 is arranged between the high-pressure part-turbine 300 and the intermediate-pressure part-turbine 303, the turbine shaft 309 having a bearing region 321 in the bearing 318. The turbine shaft 309 is mounted on a further bearing 324 next to the high-pressure part-turbine 300. In the region of this bearing 324, the high-pressure part-turbine 300 has a shaft seal 345. The turbine shaft 309 is sealed with respect to the outer casing 315 of the intermediate-pressure part-turbine 303 by two further shaft seals 345. Between a high-pressure steam inflow region 348 and a steam outlet region 351, the turbine shaft 309 in the high-pressure part-turbine 300 has the high-pressure rotor blading 354, 357. This high-pressure rotor blading 354, 357, together with the associated rotor blades (not shown in more detail), constitutes a first blading region 360. The intermediate-pressure part-turbine 303 has a central steam inflow region 333. Assigned to the steam inflow region 333, the turbine shaft 309 has a radially symmetrical shaft shield 363, a cover plate, on the one hand for dividing the flow of steam between the two flows of the intermediate-pressure part-turbine 303 and also for preventing direct contact between the hot steam and the turbine shaft 309. In the intermediate-pressure part-turbine 303, the turbine shaft 309 has a second blading region 366 comprising the intermediate-pressure rotor blades 354, 342. The hot steam flowing through the second blading region 366 flows out of the intermediate-pressure part-turbine 303 from an outflow connection piece 369 to a low-pressure part-turbine (not shown) which is connected downstream in terms of flow.

The turbine shaft 309 is composed of two turbine part-shafts 309a and 309b, which are fixedly connected to one another in the region of the bearing 318.

Figure 18:
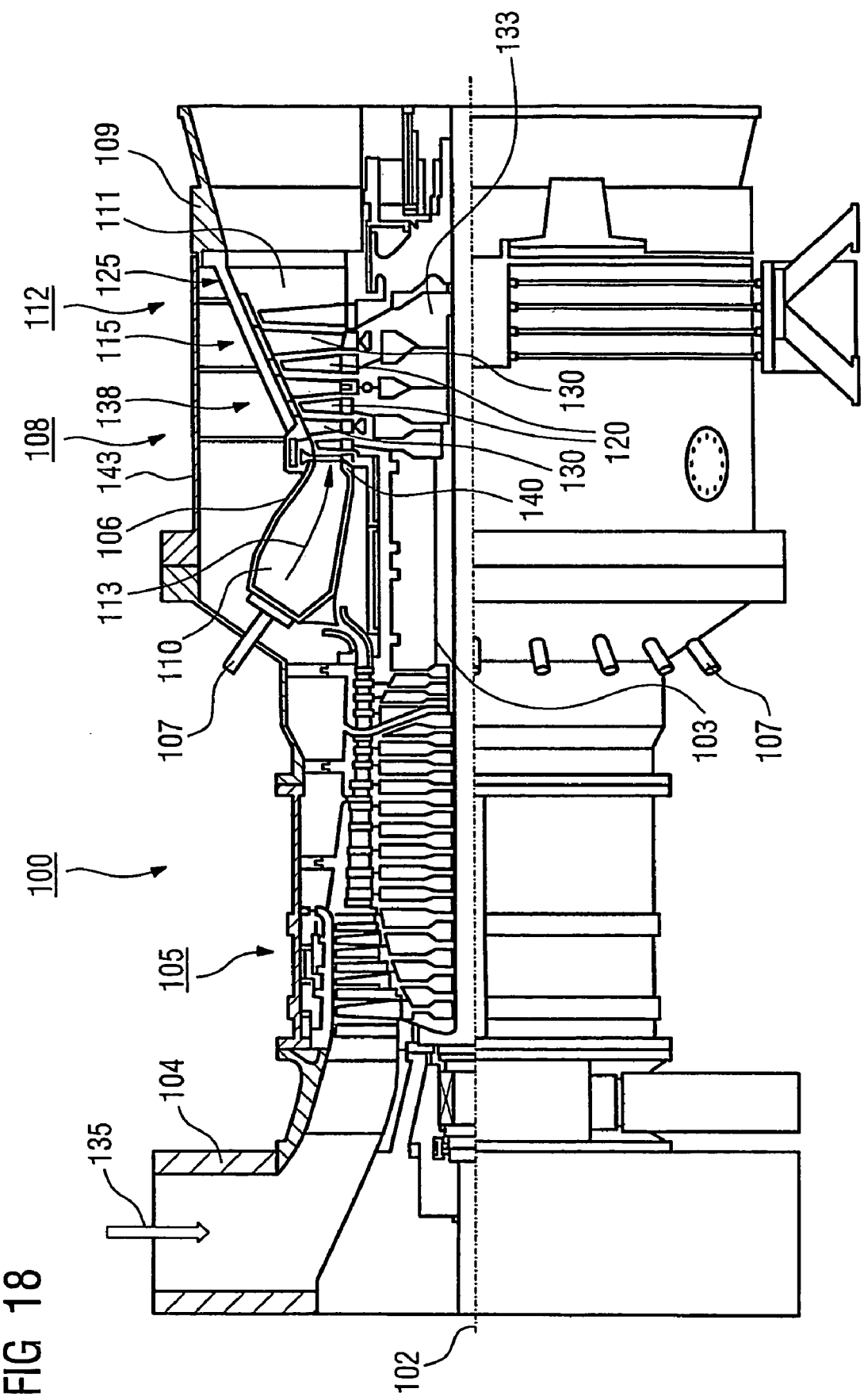
FIG. 18 shows a gas turbine.

FIG. 18 shows, by way of example, a partial longitudinal section through a gas turbine 100. In the interior, the gas turbine 100 has a rotor 103 which is mounted such that it can rotate about an axis of rotation 102 and is also referred to as the turbine rotor.

An intake housing 104, a compressor 105, a, for example, toroidal combustion chamber 110, in particular an annular combustion chamber 106, with a plurality of coaxially arranged burners 107, a turbine 108 and the exhaust-gas housing 109 follow one another along the rotor 103.

The annular combustion chamber 106 is in communication with a, for example, annular hot-gas passage 111, where, by way of example, four successive turbine stages 112 form the turbine 108.

Each turbine stage 112 is formed, for example, from two blade or vane rings. As seen in the direction of flow of a working medium 113, in the hot-gas passage 111 a row of guide vanes 115 is followed by a row 125 formed from rotor blades 120.

The guide vanes 130 are secured to an inner housing 138 of a stator 143, whereas the rotor blades 120 of a row 125 are fitted to the rotor 103 for example by means of a turbine disk 133. A generator (not shown) is coupled to the rotor 103.

While the gas turbine 100 is operating, the compressor 105 sucks in air 135 through the intake housing 104 and compresses it. The compressed air provided at the turbine-side end of the compressor 105 is passed to the burners 107, where it is mixed with a fuel. The mix is then burnt in the combustion chamber 110, forming the working medium 113.

From there, the working medium 113 flows along the hot-gas passage 111 past the guide vanes 130 and the rotor blades 120. The working medium 113 is expanded at the rotor blades 120, transferring its momentum, so that the rotor blades 120 drive the rotor 103 and the latter in turn drives the generator coupled to it.

While the gas turbine 100 is operating, the components which are exposed to the hot working medium 113 are subject to thermal stresses. The guide vanes 130 and rotor blades 120 of the first turbine stage 112, as seen in the direction of flow of the working medium 113, together with the heat shield bricks which line the annular combustion chamber 106, are subject to the highest thermal stresses.

To be able to withstand the temperatures which prevail there, they have to be cooled by means of a coolant.

The substrates may likewise have a directional structure, i.e. they are in single-crystal form (SX structure) or have only longitudinally oriented grains (DS structure). Iron-base, nickel-base or cobalt-base superalloys are used as material. By way of example, superalloys as are known from EP 1204776, EP 1306454, EP 1319729, WO 99/67435 or WO 00/44949, are used; these documents form part of the disclosure.

It is also possible for the blades or vanes 120, 130 to have coatings which protect against corrosion (MCrAlX; M is at least one element selected from the group consisting of iron (Fe), cobalt (Co), nickel (Ni), X stands for yttrium (Y) and/or at least one rare earth element) and heat by means of a thermal barrier coating. The thermal barrier coating consists, for example, of $ZrO_2$, $Y_2O_4$—$ZrO_2$, i.e. unstabilized, partially stabilized or fully stabilized by yttrium oxide and/or calcium oxide and/or magnesium oxide.

Columnar grains are produced in the thermal barrier coating by suitable coating processes, such as for example electron beam physical vapor deposition (EB-PVD).

The guide vane 130 has a guide vane root (not shown here), which faces the inner housing 138 of the turbine 108, and a guide vane head which is at the opposite end from the guide vane root. The guide vane head faces the rotor 103 and is fixed to a securing ring 140 of the stator 143.

Figure 19:
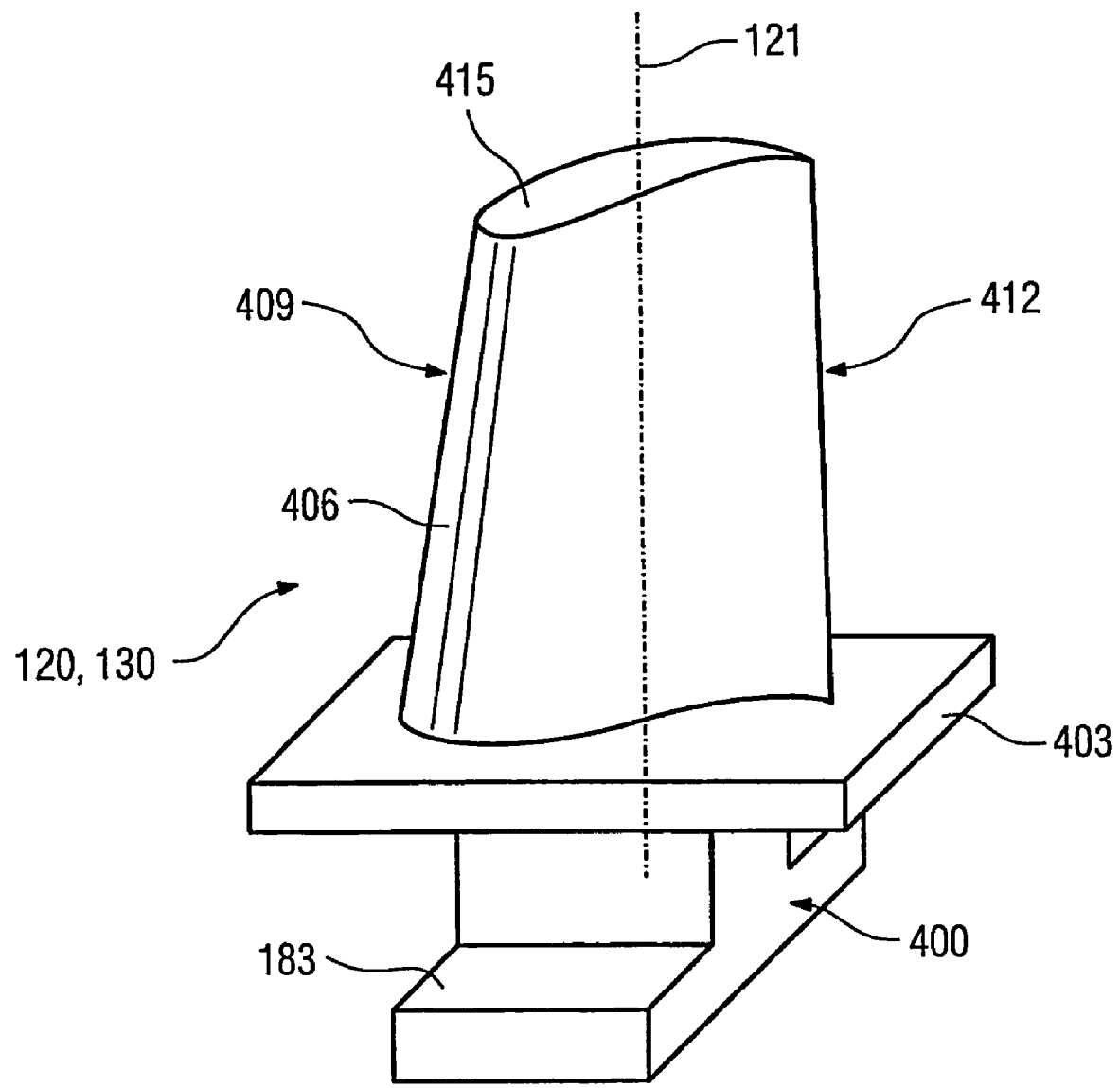
FIG. 19 shows a turbine blade or vane.

FIG. 19 shows a perspective view of a blade or vane 120, 130 which extends along a longitudinal axis 121.

The blade or vane 120 may be a rotor blade 120 or guide vane 130 of a turbo machine. The turbo machine may be a gas turbine of an aircraft or of a power plant for generating electricity, a steam turbine or a compressor.

The blade or vane 120, 130 has, in succession along the longitudinal axis 121, a securing region 400, an adjoining blade or vane platform 403 and a main blade or vane part 406. As a guide vane 130, the vane 130 may have a further platform (not shown) at its vane tip 415.

A blade or vane root 183, which is used to secure the rotor blades 120, 130 to a shaft or a disk (not shown), is formed in the securing region 400. The blade vane or vane root 183 is designed, for example, in hammerhead form. Other configurations, such as a fir-tree or dovetail root, are possible. The blade or vane 120, 130 has a leading edge 409 and a trailing edge 412 for a medium which flows past the main blade or vane part 406. In the case of conventional blades or vanes 120, 130, by way of example solid metallic materials are used in all regions 400, 403, 406 of the blade or vane 120, 130.

The blade or vane 120, 130 may in this case be produced by a casting process, also by means of directional solidification, by a forging process, by a milling process or combinations thereof.

Workpieces with a single-crystal structure or structures are used as components for machines which, in operation, are exposed to high mechanical, thermal and/or chemical stresses.

Single-crystal workpieces of this type are produced, for example, by directional solidification from the melt. This involves casting processes in which the liquid metallic alloy solidifies to form the single-crystal structure, i.e. the single-crystal workpiece, or solidifies directionally.

In this case, dendritic crystals are oriented along the direction of heat flow and form either a columnar crystalline grain structure (i.e. grains which run over the entire length of the workpiece and are referred to here, in accordance with the language customarily used, as directionally solidified) or a single-crystal structure, i.e. the entire workpiece consists of one single crystal. In these processes, a transition to globular (polycrystalline) solidification needs to be avoided, since non-directional growth inevitably forms transverse and longitudinal grain boundaries, which negate the favorable properties of the directionally solidified or single-crystal component.

Where the text refers in general terms to directionally solidified microstructures, this is to be understood as meaning both single crystals, which do not have any grain boundaries or at most have small-angle grain boundaries, and columnar crystal structures, which do have grain boundaries running in the longitudinal direction but do not have any transverse grain boundaries. This second form of crystalline structures is also described as directionally solidified microstructures (directionally solidified structures).

Processes of this type are known from U.S. Pat. No. 6,024, 792 and EP 0 892 090 A1.

Refurbishment means that after they have been used, protective layers may have to be removed from components 120, 130 (e.g. by sand-blasting). Then, the corrosion and/or oxidation layers and products are removed. If appropriate, cracks in the component 120, 130 are also repaired. This is followed by recoating of the component 120, 130, after which the component 120, 130 can be reused.

The blade or vane 120, 130 may be hollow or solid in form. If the blade or vane 120, 130 is to be cooled, it is hollow and may also have film-cooling holes (not illustrated). To protect against corrosion, the blade or vane 120, 130 has, for example, corresponding, generally metallic coatings, and to protect against heat it generally also has a ceramic coating.

Figure 20:
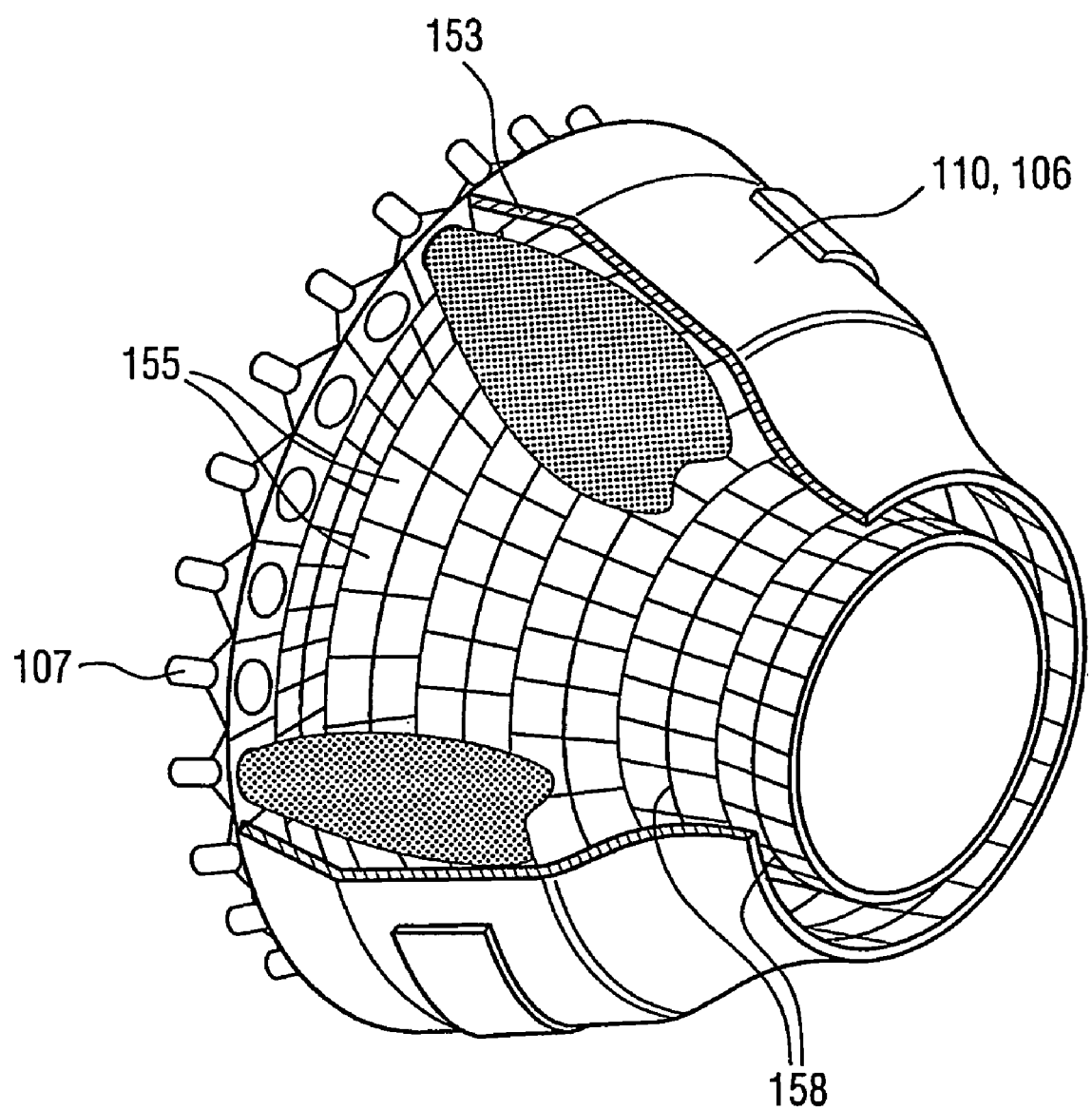
FIG. 20 shows a combustion chamber.

FIG. 20 shows a combustion chamber 110 of a gas turbine. The combustion chamber 110 is configured, for example, as what is known as an annular combustion chamber, in which a multiplicity of burners 102 arranged circumferentially around the turbine shaft 130 open out into a common combustion chamber space. For this purpose, the combustion chamber 110 overall is of annular configuration positioned around the turbine shaft 130.

To achieve a relatively high efficiency, the combustion chamber 110 is designed for a relatively high temperature of the working medium M of approximately 1000° C. to 1600° C. To allow a relatively long service life even with these operating parameters, which are unfavorable for the materials, the combustion chamber wall 153 is provided, one its side which faces the working medium M, with an inner lining formed from heat shield elements 155. On the working medium side, each heat shield element 155 is equipped with a particularly heat-resistant protective layer or is made from material that is able to withstand high temperatures. A cooling system is also provided for the heat shield elements 155 and/or their holding elements, on account of the high temperatures in the interior of the combustion chamber 110.

The materials of the combustion chamber wall and their coatings may be similar to the turbine blades or vanes.

The combustion chamber 110 is designed in particular to detect losses of heat shield elements 155. For this purpose, a number of temperature sensors 158 are positioned between the combustion chamber wall 153 and the heat shield elements 155.

The invention claimed is:

1. A method for recording microstructural changes in a layer system component of a gas turbine, comprising:
   non-destructively measuring a material parameter of the component a plurality of times at differing time points, wherein the material parameter is selected from the group consisting of: electrical capacitance, specific heat capacity, peltier coefficient, magnetic susceptibility, ferroelectricity, and pyroelectricity;
   comparing the plurality of measurements for a change in material parameter; and
   determining if a predetermined threshold percentage change in the measured material parameter is exceeded based on the comparison of the plurality of measurements.

2. The method as claimed in claim 1, wherein the first of the plurality of material parameter measurements is performed on a new component or before the first operational use of the component.

3. The method as claimed in claim 2, wherein a subsequent material parameter measurement is performed at a time interval after the first measurement and after or during the first operational use.

4. The method as claimed in claim 1, wherein the component comprises a substrate and a layer.

5. The method as claimed in claim 4, wherein the component comprises a substrate, a first layer and an outer layer.

6. The method as claimed in claim 4, wherein the material parameter measurement method is used to examine microstructural changes in the substrate or the layer of the component which are caused by:
   a change in a precipitation of the substrate or the layer material, or
   cracks in the substrate or layer.

7. The method as claimed in claim 4, wherein the substrate or the layer is an alloy and magnetic susceptibility is used to examine microstructural changes in the substrate or the layer caused by depletion of an alloying element.

8. The method as claimed in claim 7, wherein the layer is a porous ceramic layer.

9. The method as claimed in claim 8, wherein the material parameter measurement method is used to examine microstructural changes in the substrate or the layer, which are caused by a phase change in the substrate or the layer material.

10. The method as claimed in claim 9, wherein a material parameter of the combined substrate and layer is determined.

11. The method as claimed in claim 9, wherein the layer is an MCrAlX layer where M stands for at least one element selected from the group consisting of iron, cobalt or nickel and X stands for yttrium, silicon or at least one rare earth element.

12. The method as claimed in claim 4, wherein the material parameter of the substrate is determined with the layer present arranged on the substrate.

13. The method as claimed in claim 4, wherein the layer comprises a ceramic material and the material parameter is ferroelectricity or pyroelectricity of the ceramic material.

14. The method as claimed in claim 1, wherein the component is a turbine blade, vane or a lining of a combustion chamber.

15. The method as claimed in claim 1, wherein the material parameter measurement is performed on line.

16. The method as claimed in claim 1, wherein a time period is determined where the component is to be inspected, refurbished or replaced once a predefined percentage change in the material parameter is exceeded.

17. The method as claimed in claim 1, wherein the layer system comprises a ceramic and the material parameter is electrical capacitance.

18. The method as claimed in claim 1, wherein the material parameter is the peltier coefficient.

19. The method as claimed in claim 1, wherein the material parameter is the specific heat capacity.

* * * * *